(12) United States Patent
Matsue et al.

(10) Patent No.: US 8,401,259 B2
(45) Date of Patent: Mar. 19, 2013

(54) IMAGE DIAGNOSIS SUPPORT SYSTEM

(75) Inventors: Kenji Matsue, Nasushiobara (JP);
Muneyasu Kazuno, Nasushiobara (JP);
Kenichi Niwa, Otawara (JP); Akira Iwasa, Nasushiobara (JP)

(73) Assignees: Kabushiki Kaisha Toshiba, Tokyo (JP);
Toshiba Medical Systems Corporation, Otawara-shi (JP)

( * ) Notice: Subject to any disclaimer, the term of this patent is extended or adjusted under 35 U.S.C. 154(b) by 660 days.

(21) Appl. No.: 12/100,736

(22) Filed: Apr. 10, 2008

(65) Prior Publication Data
US 2008/0253628 A1 Oct. 16, 2008

(30) Foreign Application Priority Data
Apr. 12, 2007 (JP) ................................. 2007-105331

(51) Int. Cl.
*G06K 9/00* (2006.01)
(52) U.S. Cl. ...................................................... 382/128
(58) Field of Classification Search .................... 382/128
See application file for complete search history.

(56) References Cited

U.S. PATENT DOCUMENTS

| | | | |
|---|---|---|---|
| 7,607,079 B2 * | 10/2009 | Reiner ........................... | 715/233 |
| 2005/0154614 A1 * | 7/2005 | Swanson et al. .................. | 705/3 |
| 2005/0226405 A1 * | 10/2005 | Fukatsu et al. .................... | 380/1 |
| 2006/0025670 A1 * | 2/2006 | Kim et al. ....................... | 600/407 |
| 2006/0277073 A1 * | 12/2006 | Heilbrunn et al. ................. | 705/3 |
| 2007/0140538 A1 * | 6/2007 | Doran et al. ..................... | 382/128 |
| 2007/0238963 A1 | 10/2007 | Kaminaga et al. | |
| 2007/0239489 A1 | 10/2007 | Masuzawa et al. | |
| 2009/0110251 A1 * | 4/2009 | Hoffman et al. .............. | 382/129 |
| 2009/0228370 A1 * | 9/2009 | Shakkarwar .................... | 705/26 |
| 2010/0076789 A1 * | 3/2010 | Pan .................................. | 705/3 |

FOREIGN PATENT DOCUMENTS

| | | |
|---|---|---|
| JP | 2002-132557 | 5/2002 |
| JP | 2002-169898 | 6/2002 |
| JP | 2002-304467 | 10/2002 |
| JP | 2004-216007 | 8/2004 |
| JP | 2006-260300 | 9/2006 |
| JP | 2007-68787 | 3/2007 |
| JP | 2007-167634 | 7/2007 |

OTHER PUBLICATIONS

U.S. Appl. No. 12/032,006, filed Feb. 15, 2008, Hiroshi Fukatsu et al.
U.S. Appl. No. 12/032,266, filed Feb. 15, 2008, Hiroshi Fukatsu et al.
U.S. Appl. No. 12/107,356, filed Apr. 22, 2008, Kazuno, et al.
Office Action issued Apr. 17, 2012 in Japanese Patent Application No. 2007-105331 (with English translation).

* cited by examiner

*Primary Examiner* — Bhavesh Mehta
*Assistant Examiner* — Utpal Shah
(74) *Attorney, Agent, or Firm* — Oblon, Spivak, McClelland, Maier & Neustadt, L.L.P.

(57) ABSTRACT

The admission of the editing of information on a key image of an object, the type of edit processing, and the contents targeted for edit processing are controlled in accordance with a combination of user information and device information (i.e., a scene where the key image is used).

8 Claims, 7 Drawing Sheets

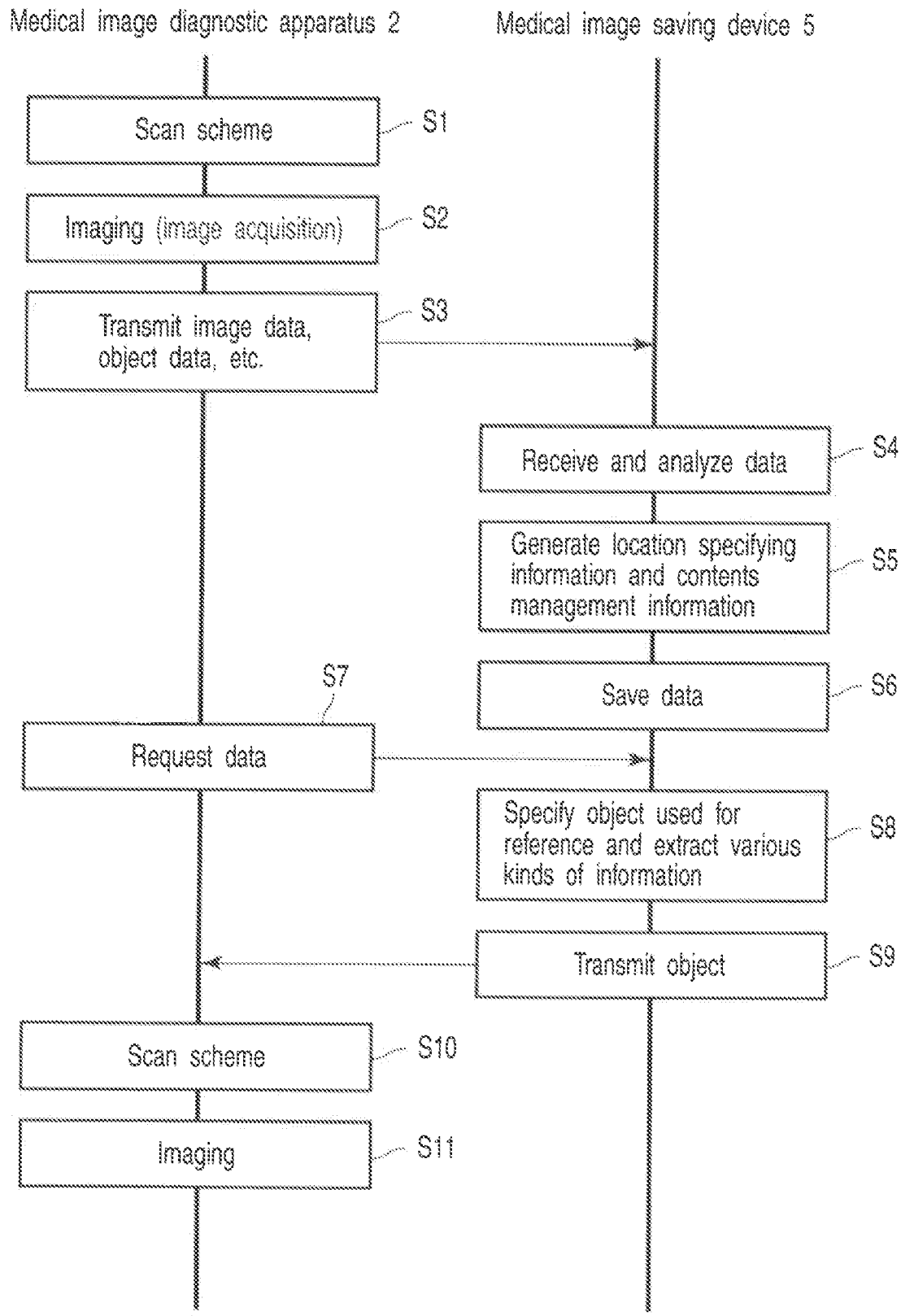
F I G. 3

|  | Medical report creartion support system (Report Viewer) | Medical image observation device (Image Viewer) |
|---|---|---|
| Dr.A | Update / addition | Update / addition |
| Dr.B | - | - |
| Dr.C | - | - |
| Prof.D | New / update / addition | Update / addition |
| Dr.E | New | - |

FIG. 6

|  | New | Update | Addition |
|---|---|---|---|
| Medical report generartion support system (Report Viewer) | · Image UID<br>· Viewer type<br>· Report UID<br>· History management number | · Image UID<br>· Viewer type<br>· Report UID<br>· History management number | · Image UID<br>· Report UID<br>· History management number |
| Medical image observation device (Image Viewer) |  | · Image UID<br>· Viewer type "Image Viewer<br>· History management number | · Image UID<br>· Viewer type "Image Viewer<br>· History management number |
| ⋮ |  |  |  |

FIG. 7

IMAGE DIAGNOSIS SUPPORT SYSTEM

CROSS-REFERENCE TO RELATED APPLICATIONS

This application is based upon and claims the benefit of priority from prior Japanese Patent Application No. 2007-105331, filed Apr. 12, 2007, the entire contents of which are incorporated herein by reference.

BACKGROUND OF THE INVENTION

1. Field of the Invention

The present invention relates to a system for managing, in an examination carried out using a medical image diagnostic apparatus, an object which has, as its contents, information set in the apparatus in imaging (imaging information), a positioning image used in the imaging, information on an image (key image) serving as a basis in a past diagnosis, information on the past examinations referred to in the imaging, etc.

2. Description of the Related Art

Recently, the special field of medical practice is segmentized. For example, an image diagnosis is separated into various tasks, such as the acquisition of a diagnostic image of a patient, the interpretation of the acquired diagnostic image and the generation of a report, and the explanation of a diagnostic result based on the result of the report and a treatment policy. Each task is taken charge of by each specialist (a doctor or engineer in charge), and all these tasks achieve the medical practice such as a diagnosis toward the patient. Each specialist performs each task properly referring to, for example, information on the past diagnosis on the basis of information generated by other specialists in the previous tasks. These tasks are carried out in, for example, an X-ray CT apparatus for acquiring the diagnostic image, a medical image diagnostic apparatus such as an MRI apparatus, a medical image saving device for storing the diagnostic images, a medical image observation device for the interpretation of the diagnostic image, a medical report generation support system, etc.

Recently, there has been proposed a system for allowing the efficient use of past examination information in the above-mentioned image diagnosis with the segmentized tasks, as described in, for example, Jpn. Pat. Appln. No. 2006-319356. In this system, an object is generated for each examination or for each series and shared, and the object can be referred to in any device with any timing. This makes it possible for a user to know, for example, imaging conditions used in a past examination or a key image in a past diagnosis, and reproduce the past examination with high accuracy, or accurately recognize the key image used in the past diagnosis or its position.

The contents of this object can be freely arranged as needed. Particularly in clinical scenes, it is desired that information for identifying the past key image (e.g., the latest key image) or the key image itself be included in the object as much as possible so that there will be no cases where a part which seems to be most significant can not be photographed in the imaging to be carried out in the future.

However, for example, the following problems may occur if the information for identifying the key image or the key image itself is included in the object.

That is, there is no agreement on the point of deciding the key image to be included in the object, and there are variations in the environment (e.g., a hospital) into which the system is introduced. For example, in an actual medical scene, the key image may be subjected to a correction, addition or modification by the same doctor or a plurality of doctors for one examination. In such a case, there may be inconsistency such as the disagreement between a key image serving as the basis of a diagnosis and a key image specified by the object, depending on the way of determining the timing for deciding the key image (or information for specifying the key image) to be included in the object.

BRIEF SUMMARY OF THE INVENTION

The present invention has been made in view of such circumstances, and is directed to provide an image diagnosis support system capable of always conforming a key image serving as the basis of a diagnosis to, for example, a key image specified by information included in an object.

According to an aspect of the present invention, there is provided an image diagnosis support system comprising: a storage unit which stores a plurality of objects, the objects being configured to include, as contents thereof, information on a diagnostic image serving as a basis in a diagnosis based on an examination, the objects managing information used in the examination; an acceptance unit which accepts, from a device involved in the generation of a medical report, examination specifying information to specify an examination or series corresponding to the medical report, and edit information on the diagnostic image; and an editing unit which edits and updates information on the diagnostic image of the object specified by the examination specifying information, in accordance with the edit information.

According to another aspect of the present invention, there is provided an image diagnosis support system comprising: a storage unit which stores a plurality of objects including, as contents thereof, information on a diagnostic image serving as a basis in a diagnosis based on an examination, the storage unit also storing a table to manage the admission of the edit processing of information on the diagnostic image included in the object for each combination of user information to specify a user involved in the generation of a medical report and device information to specify a device used for the generation of the medical report; an acceptance unit which accepts the user information and the device information from the device involved in the generation of the medical report; a determination unit which determines, on the basis of the table, whether to admit the edit processing of the information on the diagnostic image included in the object with regard to the combination of the accepted user information and device information; and a transmission unit which transmits the result of the determination to the device involved in the generation of the medical report.

BRIEF DESCRIPTION OF THE SEVERAL VIEWS OF THE DRAWING

FIG. 3 is a flowchart showing one example of the flow of processing including the generation, analysis and saving of the object;

FIG. 6 shows one example of an edit processing table;

FIG. 7 shows one example of an edit target table; and

DETAILED DESCRIPTION OF THE INVENTION

Embodiments of the present invention will hereinafter be described with reference to the drawings. It is to be noted that the same signs are assigned to components having about the same function and configuration in the following description, and repetitive explanations are only given when necessary.

In addition, in the present embodiment, an example is described where a medical image saving device comprises an image diagnosis support function described later. However, this is not a restriction, and other medical instruments such as a medical report generation support system and a medical image observation device may be configured to comprise the image diagnosis support function.

Figure 1:
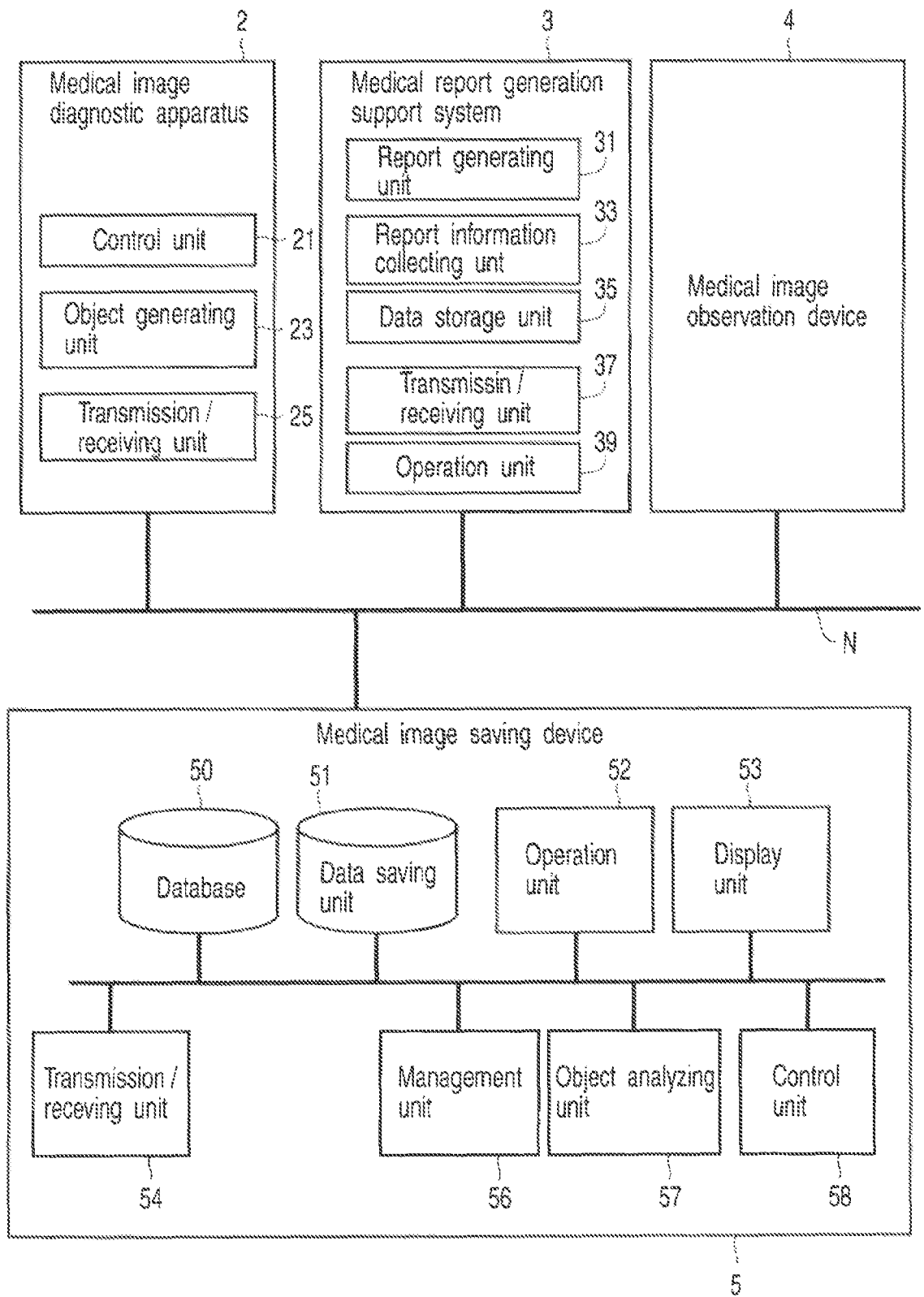
FIG. 1 is a diagram showing the configuration of an in-hospital network system 1 which realizes an image diagnosis support system according to a first embodiment.

FIG. 1 is a diagram showing the configuration of an in-hospital network system 1 which realizes an image diagnosis support system according to the present embodiment. As shown, the present in-hospital network system 1 comprises a medical image diagnostic apparatus 2, a medical report generation support system 3, a medical image observation device 4 and a medical image saving device 5.

[Medical Image Diagnostic Apparatus]

The medical image diagnostic apparatus 2 is an image diagnostic apparatus such as an X-ray computerized tomographic apparatus (X-ray CT apparatus), a magnetic resonance imaging apparatus, an ultrasonic diagnostic apparatus, a nuclear medicine diagnostic apparatus or an X-ray diagnostic apparatus. The present embodiment assumes that the medical image diagnostic apparatus 2 is the X-ray CT apparatus so that the explanation may be specific.

Furthermore, in addition to the photographic system for acquiring a diagnostic image of a patient, the medical image diagnostic apparatus 2 comprises a control unit 21, an object generating unit 23, a transmission/receiving unit 25, a display unit, a data storage unit, and an operation unit (those without reference signs are not shown), etc.

The control unit 21 performs overall control of the static or dynamic operation of the present medical image diagnostic apparatus 2.

The object generating unit 23 generates an object. The object is generated as an entity (e.g., a file) of information separate from ordinary image data, and stored and managed. It is to be noted that the configuration of this object is described layer in detail.

The transmission/receiving unit 25 receives from other equipment or transmits to the other equipment medical information such as an image or the object via a network N.

[Medical Report Generation Support System]

The medical report generation support system 3 is a device for supporting a user in the generation of a report, and has a report generating unit 31, a report information collecting unit 33, a data storage unit 35, a transmission/receiving unit 37 and an operation unit 39.

The report generating unit 31 generates a report including patient information, examination information (such as an examination UID (unique ID), a series UID and a report UID), information for specifying an image (key image) serving as the basis of a diagnosis (e.g., an image UID or a place to store the image), observations by a doctor who has made an interpretation on the basis of the key image. The report which is being generated or which has been generated is displayed in a predetermined form on an unshown display unit.

The report information collecting unit 33 collects various kinds of information necessary for the generation of the report from a predetermined device (e.g., a report database) via the network. Further, in response to a predetermined operation performed using the operation unit 39, the report information collecting unit 33 transmits, to the medical image saving device 5, an instruction to edit information for specifying the user who has generated the report (user information), information for specifying the medical report generation support system used for the generation of the medical report (device information), information on the key image used for the report generation (i.e., information including at least one of entity data for the key image, information for specifying the key image and information on the position in a subject in the key image), and information on the key image in the object.

The data storage unit 35 stores the report generated by the report generating unit 31.

The transmission/receiving unit 37 receives from the other equipment or transmits to the other equipment medical information such as images, information used for the generation of the report and report data via a network N. Further, at the time of the generation of the report, the transmission/receiving unit 37 transmits, to the medical image saving device 5, information on the edit processing of the key image (e.g., parameter setting values concerning the addition of a new key image, the deletion of the existing key image, a change to another key image and image processing of the key image. This is hereinafter referred to as "key image edit information".), and information for specifying an examination or series at which the report is aimed (or an examination or series in which the key image has been acquired) (examination specifying information).

The operation unit 39 is a device which comprises, for example, a keyboard, various switches and a mouse, and which is capable of inputting instructions from an operator. Further, the operation unit 39 has a decision button for instructing to decide the contents of the report (i.e., decide the key image), and a button for instructing to edit the key image. Still further, the operation unit 39 has a button (e.g., a GUI) for instructing on the kind of edit processing to be performed for (i.e., the type of edit processing) the information on the key image of the object (a plurality of objects in some cases) corresponding to the examination (or series) that corresponds to a report, if any, whose contents have been decided.

It is to be noted that the configuration of the medical report generation support system 3 shown in FIG. 3 is one example. Therefore, the medical report generation support system 3 is not limited to this configuration, and may be constructed by, for example, a client-server system concerned with the generation of the report. In such a case, the report information collecting unit 33 may be provided on any of the client side or server side.

[Medical Image Observation Device]

The medical image observation device 4 is used, for example, when a doctor generates a report while interpreting an image, and displays the image read from the medical image saving device 5 as it is, or subjects the image to predetermined image processing to generate a diagnostic image and displays the diagnostic image. Further, the medical image observation device 4 generates an object for the effective use of conditions (e.g., image generation conditions) used in, for example, post-processing for generating the diagnostic image.

In addition, the medical image observation device 4 and the medical report generation support system 3 are separately configured in the present embodiment. However, this is not a restriction, and the medical image observation device 4 and the medical report generation support system 3 may be configured as one device.

[Medical Image Saving Device]

The medical image saving device 5 manages and stores images generated in the medical image diagnostic apparatus 2, images generated by post-processing in the medical image observation device 4. etc., in association with patient IDs, series IDs, etc. Further, the medical image saving device 5 analyzes the object generated in the medical image diagnostic apparatus 2, and saves various kinds of data in predetermined places. Still further, the medical image saving device 5 operates as the image diagnosis support system which realizes the image diagnosis support function described later. Here, the image diagnosis support function according to the present embodiment edits information on the key image of the object saved in the medical image saving device 5 in conjunction with, if any, the edit processing of the key image on the side of the medical report generation support system 3 so that the image actually treated as the key image during the generation of the report may conform to the key image specified by information on the key image of the object.

The present medical image saving device 5 comprises a database 50, a data saving unit 51, an operation unit 52, a display unit 53, a transmission/receiving unit 54, a management unit 56, an object analyzing unit 57 and a control unit 58.

The database 50 is a database which manages information for managing the kinds of information included in the respective objects (contents management information), and information for specifying the saving places (locations) of the entity data for various images and the entity data regarding various kinds of information included in the objects (location specifying information).

The data saving unit 51 receives various kinds of data such as image data and the objects via the transmission/receiving unit 54, and writes and saves them in appropriate places. Further, when the places to save the various kinds of data are decided or when the various kinds of data are deleted or modified, the data saving unit 51 communicates with the database 50, and corrects the contents management information and the location specifying information managed by the database 50. In addition, this data saving unit 51 does not necessarily have to be incorporated in the medical image saving device 5, and may be in another place on the network.

The operation unit 52 is a device which comprises, for example, a keyboard, various switches and a mouse, and which is capable of inputting instructions from the operator.

The display unit 53 is a monitor for displaying an operation screen and predetermined images.

The transmission/receiving unit 54 receives from the other equipment or transmits to the other equipment medical information such as images and the objects via the network N. Further, the transmission/receiving unit 54 receives the edit information on the key image from the medical report generation support system 3.

The management unit 56 searches the data saving unit 51 on the basis of the examination specifying information received from the medical report generation support system 3, and extracts an object corresponding to the examination. Further, the management unit 56 edits and updates the information on the key image included in the object corresponding to the examination, on the basis of the edit information received from the medical report generation support system 3.

The object analyzing unit 57 determines whether data received from the medical image diagnostic apparatus 2, the medical report generation support system 3, the medical image observation device 4, etc. are object data or normal image data, and saves the various kinds of data in the predetermined places of the data saving unit 51 and also generates location specifying information associated with the various kinds of data. Further, the object analyzing unit 57 analyzes the received object, and generates the contents management information associated with the object.

The control unit 58 performs overall control of the static or dynamic operation of the present medical image saving device 5. Further, the control unit 58 uncompresses a dedicated program stored in the data saving unit 51 on an unshown memory to realize the image diagnosis support function described later, etc. Still further, in response to requests from the medical image diagnostic apparatus 2, the medical report generation support system 3, the medical image observation device 4. etc., the control unit 58 searches the database 50 and the data saving unit 51 for target entity data (image datan object data) and information for specifying the locations of various kinds of data (location specifying information), and transmits them via the network.

(Object)

Figure 2:
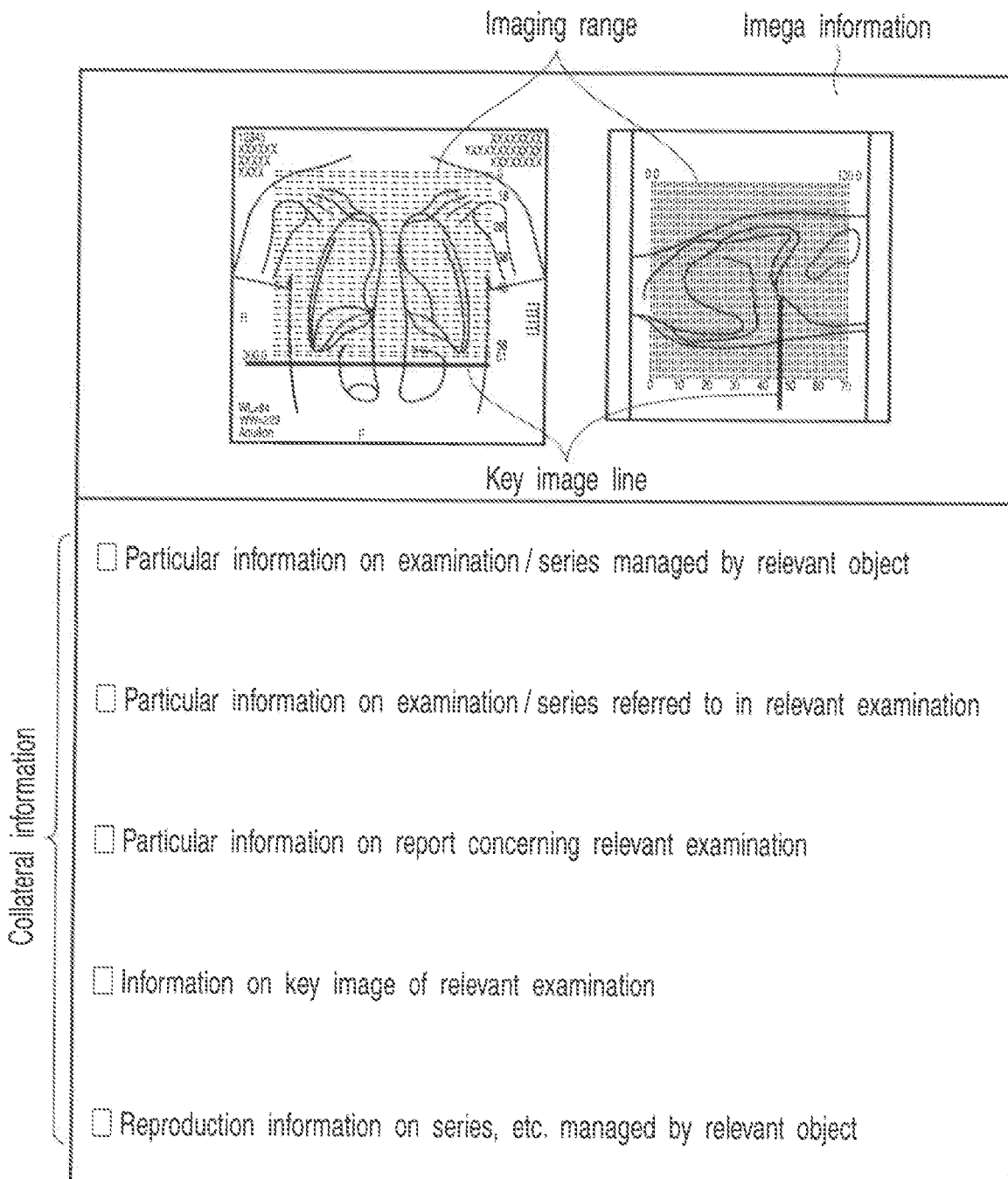
FIG. 2 is a diagram showing one example of the configuration of an object.

Next, the object is explained. The object is composed of image information and incidental (character or numerical) information and generated, for example, for each examination or for each series, in order to effectively use information used when a medical practice has taken place (e.g., a positioning image, an imaging position, an imaging range, imaging conditions, image generation conditions, information on the key image, information on the report, etc.), for example, as shown in FIG. 2. In addition, the series classifies information with signs indicating time (when the information has been generated), space (where the information has been generated) and clinical characteristics of the information (what kind of clinical significance the information has).

[Image Information]

The image information included in the object is one or a plurality of positioning images for referring to a position or range (e.g., a scanogram used in the X-ray CT apparatus, a coronal image produced by a pilot scan in an MRI apparatus, etc. Also referred to as a "scout image" or "localizer"). Here, the range is a physical range targeted by a detector for a signal detection or image generation based on energy actually supplied by the medical image diagnostic apparatus on, for example, an X-ray or high frequency. For example, the range is a range in the direction of a body axis reconstructed on the basis of projection data detected by the detector (reconstruction range) in the case of the X-ray CT apparatus, and is a scan range in the case of the MRI apparatus. The range is generally clearly indicated by, for example, a dotted line on the positioning image acquired before a scan, and may be indicated together with a line showing an image generation pitch in the direction of the body axis. Moreover, in this image information, if necessary, a marker indicating the position of the key image may be included on the positioning image, and the key image itself (entity data for the key image) may be included.

In addition, when the edit processing is admitted in the image diagnosis support function described later, the entity data for the key image, the position of the key image on the positioning image, etc. that are managed as the image information are edited in accordance with an edit instruction received from the medical report generation support system 3.

[Incidental Information]

The incidental information included in the object can be roughly classified into five kinds: particular information on the examination/series corresponding to the object; particular information on the examination/series referred to in the examination; particular information on the report concerning the examination corresponding to the object; information on the key image of the examination corresponding to the object; and reproduction information on the examination/series corresponding to the object. Each kind of the information is explained below.

[Incidental Information 1: Particular Information on the Examination/Series Corresponding to the Object]

This incidental information is information for differentiating the object from other objects, and includes an identifier of the (shared) object (object UID), an identifier of the series targeted for management (management target series UID) and an identifier of the examination targeted for management (management target examination UID).

The object UID is information for differentiating (specifying) the object from other objects, and is issued by an object generator in each device in a system which does not overlap at the time of the generation of the object. The management target series UID and the management target examination UID are information for specifying the series and examination targeted for management by the object.

[Incidental Information 2: Particular Information on the Examination/Series Referred to in the Examination]

This incidental information is information for indicating the association of the object with other objects, and includes a parent (shared) object identifier (parent object UID), a related series identifier (related series UID), a UID of the series and a related examination identifier.

The parent object UID is information for specifying an object (parent object) referred to when the object is generated. The related series UID is information for specifying a series which uses the same conditions (e.g., the imaging conditions, the positioning image, etc.) as those of the object. Due to the nature of the related series UID, there may be a plurality of related series UIDs in object peculiar information. At the same time, it is preferable to attach, for example, incidental information for the series (series date and time, a series number, a series description, the type of imaging) in association with the series UID. The series UID is an identifier for specifying a series for which the imaging conditions, etc. are indicated by the object.

In addition, the data specified by each UID makes it possible to quickly trace back the examination process of the derivation of its image group by an access to liked data and thus to data linked in accordance with each UID. Moreover, the date and time on which the object has been generated may be included in the object peculiar information.

[Incidental Information 3: Particular Information on the Report Concerning the Examination]

This incidental information is an identifier for specifying a report generated in the examination (report identifier). In addition, with regard to a given examination, a report once generated may be corrected later or a new report may be separately generated. When different identifiers are issued for these reports, the incidental information includes all the report identifiers or the report identifiers selected in accordance with predetermined condition.

[Incidental Information 4: Information on the Key Image of the Examination]

This incidental information is information for specifying the information to specify a key image used in interpretation or an image diagnosis in a component on the side of the medical image saving device 5 (e.g., an SOPInstanceUID of a DICOM standard), the entity data for the key image, and the position and direction of the key image (e.g., information such as a z-axis coordinate position, a direction during observation, magnification and WW/WL). Moreover, when the key image is an MPR image, the incidental information may include the position and direction, generation conditions, etc. for the MPR image to serve as the key image, in the same manner as the image generation conditions.

In the image diagnosis support processing described later, the admission of edit processing and the type of edit processing are determined in accordance with the combination of a user who has generated the report and a device used for the generation of the report, and the incidental information is managed in accordance with the result of the determination.

[Incidental Information 5: Reproduction Information on the Series, Etc. Managed by the Object]

This incidental information is information for reproducing processing performed in the past examination or series, and includes the imaging conditions, the image generation conditions, etc.

The imaging conditions are physical conditions needed by an imaging operation to collect physical data serving as the basis for image generation from a patient. The contents of the conditions are dependent on the kind of modality. For example, the imaging conditions of the X-ray CT apparatus are physical amounts such as the start position and range of a scan (the movement amount of a bed), KV/mA of an X-ray tube, and a bed movement amount per revolution relative to the total width of an obtained image slice (beam pitch). However, the contents of the imaging conditions are not restricted to this example. For example, the imaging conditions may be configured to include the insertion direction of a subject during the examination (information on whether the subject enters the apparatus feet first or head first), the administration of contrast media, the amount of administration, the kind of a drug, the body position of the patient (the direction in which the patient lies in a diagnosis, the posture), etc. Moreover, there has been recently a function to automatically control KV/mA to produce a uniform image quality for the reduction of radiation exposure. In such a case, image noise (an SD value) which is a control amount may be configured to be included in the imaging conditions.

Furthermore, in the case of the MRI apparatus, the imaging conditions can include parameters such as the imaging range, the insertion direction and body position of the patient, magnetic field intensity, a pulse sequence, the kind of a detection coil, the place to install the detection coil, the presence of electrocardiographic synchronization or respiratory synchronization, the presence of a bed ventilator, a body part in the center of imaging, and the installation position.

The image generation conditions are parameters for reconstructing an image from the physical data obtained by imaging, and are filtering parameters such as a reconstruction range, a time phase, and the position of the image, a direction, a thickness, an FOV (magnification) and a reconstruction function. The image generation conditions also include conditions used in image processing such as volume rendering and MPR processing performed in the various kinds of medical image diagnostic apparatuses and image reference apparatuses. For example, in the case of the MPR processing, reference coordinates and a normal vector, a slice thickness, a range, etc. correspond to the image generation conditions.

In addition, the range of reconstruction conditions may be defined by attaching a positioning image indicating the reconstruction range. In such a case, a plurality of positioning images indicating a plurality of reconstruction ranges are stored in one object.

The maintenance of the above-mentioned incidental information makes it possible to properly take all the images comparable with a previous image at the start of examination and interpretation. In addition, the object does not have to have all the information mentioned above, and the contents of the object can be variously modified depending on the apparatus used or the purpose as long as the information used when a medical practice has taken place can be effectively utilized. For example, the object used for the medical image diagnostic apparatus (modality) can also be composed of a patient ID, position information concerning a scan range (reconstruction range), incidental information consisting of landmarks, and a reference image as image information. Moreover, the object used in a PACS may be composed of a patient ID, incidental information consisting of the position information for the key image and landmarks, and a reference image as image information. Further, when the reference image is not needed and a specification for simply using, for example, past imaging conditions is desired, an object can be generated with a configuration which only comprises incidental information including the imaging conditions, etc.

FIG. 3 is a flowchart showing one example of the flow of processing including the generation, analysis and saving of the object. As shown, in the medical image diagnostic apparatus 2, a scan scheme is first carried out referring to, for example, the past object, such that imaging (image acquisition) is performed (steps S1, S2). The object generating unit 23 generates an object on the basis of patient information, the object used for reference, the positioning image used in the imaging, the imaging conditions, etc. The transmission/receiving unit 25 transmits the image data acquired by the imaging and data on the generated object to the medical image saving device 5 via the network (step S3).

Then, the object received by the transmission/receiving unit 54 is analyzed in the object analyzing unit 57 (step S4), and location specifying information and contents management information associated with the object are generated (step S5). Further, entity data for the object is saved in a predetermined place in the data saving unit 51 (step S6).

The saved object is used as reference data in, for example, future imaging. That is, when a request for the object data is transmitted from the transmission/receiving unit 25 to the medical image saving device 5 (step S7), the control unit 58 specifies an object used for reference on the basis of, for example, the patient information, etc. and the contents management information. Further, the control unit 58 searches the data saving unit 51 using a location information table, and extracts various kinds of information to be included in the object (step S8). The extracted various kinds of information are transmitted to the medical image diagnostic apparatus 2 as objects for reference (step S9). The medical image diagnostic apparatus 2 receives the object, and carries out the scan scheme referring to the object, such that imaging (image acquisition) is performed (steps S10, S11).

(Image Diagnosis Support Processing)

Next, the processing using the image diagnosis support function executed in the medical image saving device 5 according to the present embodiment (image diagnosis support processing) is described. When a key image in a report is edited in the medical report generation support system 3, the image diagnosis support processing according to the present embodiment automatically reflects the result of the edit processing in information on the key image included in the object managed in the medical image saving device 5.

Figure 4:
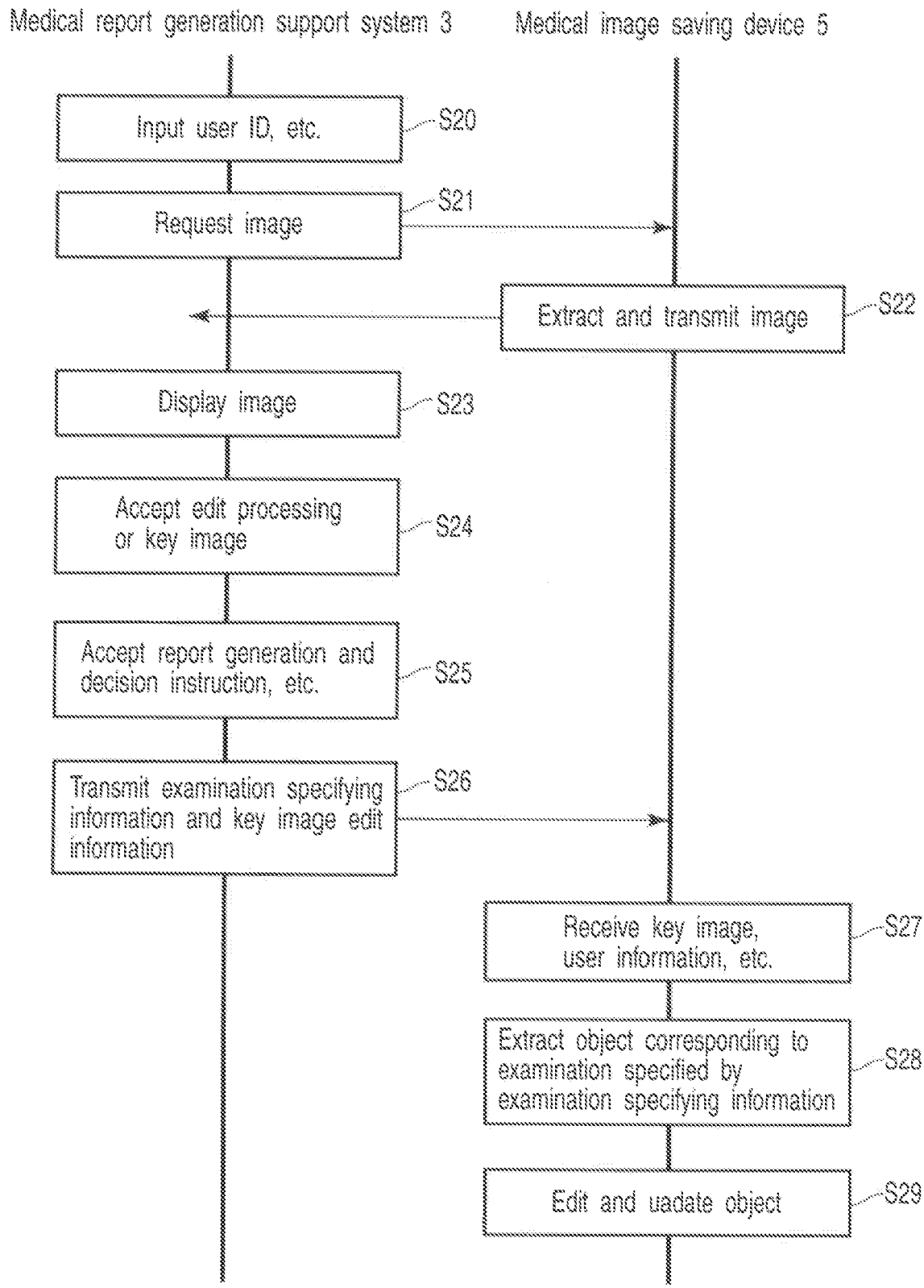
FIG. 4 is a flowchart showing the flow of image diagnosis support processing according to the first embodiment.

FIG. 4 is a flowchart showing the flow of the image diagnosis support processing according to the first embodiment. As shown, the user who has generated the report first inputs, for example, his own ID to log into the medical report generation support system 3, and also inputs a UID of the examination targeted for report generation, thereby acquiring information necessary for the report generation (e.g., personal data on the patient) via the network N (step S20).

Then, a request for an image for use in the report generation is transmitted from the transmission/receiving unit 37 of the medical report generation support system 3 to the transmission/receiving unit 54 of the medical image saving device 5 (step S21). The control unit 58 searches the data saving unit 51 with reference to the location specifying information, and extracts the requested image and transmits the image to the medical report generation support system 3 (step S22). In the medical report generation support system 3, the transmitted images are sequentially displayed (step S23). The report generating unit 31 accepts an instruction to select an image usable as the key image and an instruction on various kinds of editing of the key image, from the operator observing the displayed images via the operation unit 39 (step S24).

Then, when an instruction to decide the key image is input via the operation unit 39 (step S25), examination specifying information and key image edit information are transmitted to the medical image saving device 5 (step S26).

In addition, a trigger for the transmission of the key image edit information, etc. to the medical image saving device 5 is not restricted to the above-mentioned processing of deciding the report contents, and may be any trigger as long as it is an operation in which the user himself intentionally instructs to decide the key image. For example, it may be an operation of determining a particular image displayed in the medical report generation support system 3 or the medical image observation device 4 to be the key image (e.g., the operation of the decision button), an operation to affix the image to the report, an operation of associating the image with report sentences (hyperlink) or an operation to decide a report.

When the examination specifying information and the key image edit information are received by the transmission/receiving unit 54 of the medical image saving device 5 (step S27), the management unit 56 searches the data saving unit 51 in accordance with the examination specifying information received from the medical report generation support system 3, and extracts an object corresponding to the examination specified by the above-mentioned information (step S28). Further, the management unit 56 edits the information on the key image included in the extracted object (a plurality of objects in some cases) on the basis of the key image edit information received from the medical report generation support system 3, and overwrites the edited information to update the object (step S29).

(Effects)

The following effects can be obtained according to the configuration described above.

According to the present image diagnosis support system, when the key image in the report is edited in the medical report generation support system 3, the contents of the edit processing are automatically reflected in the information on the key image included in the object managed in the medical image saving device 5. It is thus possible to link, in the medical report generation support system 3, the edit processing of the key image in the report with the edit processing of the information on the key image in the object. As a result, it is possible to automatically conform the image actually treated as the key image during the generation of the report to the image specified by the information on the key image in the object, such that a highly reliable object can be generated. Moreover, the key image in the past examination can be rapidly and accurately specified using the object at the time of, for example, imaging or interpretation and a diagnosis, and it is also possible to prevent an error caused by the confusion of key images.

SECOND EMBODIMENT

Next, a second embodiment of the present invention is described. The present embodiment controls and manages the admission of the editing of information on a key image of an object, the type of the edit processing, and the contents targeted for edit processing in accordance with a combination of user information and device information (i.e., a scene where the key image is used) so that an image actually treated as the key image during the generation of a report may conform to a key image specified by information on the key image of the object.

Figure 5:
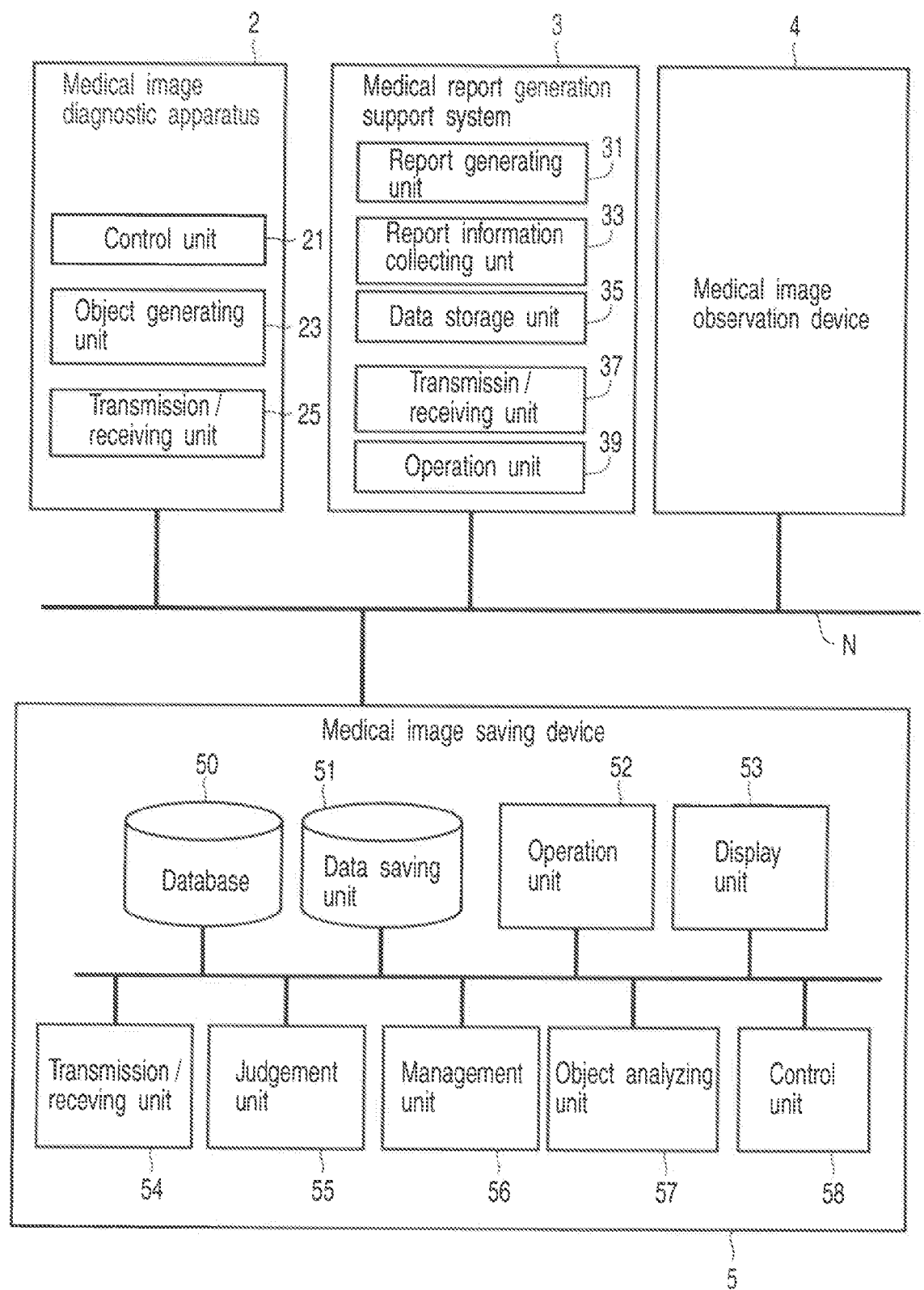
FIG. 5 is a diagram showing the configuration of an in-hospital network system 1 which realizes an image diagnosis support system according to a second embodiment.

FIG. 5 is a diagram showing the configuration of an in-hospital network system 1 which realizes an image diagnosis support system according to the second embodiment. By comparison with FIG. 1, the configuration of a medical image saving device 5 is different.

Furthermore, a database 50 stores an edit processing table and an edit target table used in the image diagnosis support function.

Here, the edit processing table defines the admissible edit processing of information on the key image in the object targeted for the management of an examination corresponding to the report in accordance with the combination of a user and a device. Moreover, the edit target table defines an item of the information on the key image targeted for edit processing for each kind of edit processing.

FIG. 6 shows one example of the edit processing table. In this example, the edit processing is sorted into three kinds: new, update and addition. The "new" is processing for newly registering the information on the key image when there is no information on the key image in the object. The "update" is processing for replacing the information on the key image already registered in the object with information on another key image. This is used as a correction function when the user is confident that the key image has been mistaken, for example, in the case where second interpretation is conducted by an interpreting doctor in a position to correct first interpretation or in the case where the user intends to declare the use of this edit processing. The "addition" is processing for adding another new information without making any change in the already registered information.

FIG. 7 shows one example of the edit target table. As shown, when, for example, the edit processing "new" is indicated from the medical report generation support system and admitted, a "key image UID", a "viewer (device) kind", a "report UID" and a "history management number" are registered in the existing object as new contents. Further, when, for example, the edit processing "update" is indicated from the medical report generation support system and admitted, the various kinds of information including the "key image UID", "viewer (device) kind", "report UID" and "history management number" already registered in the existing object are replaced on the basis of information received from the medical report generation support system 3. Still further, when, for example, the edit processing "addition" is indicated from the medical report generation support system and admitted, the various kinds of new information including the "key image UID", "report UID" and "history management number" are added to the contents already registered in the existing object on the basis of the information received from the medical report generation support system 3.

A determination unit 55 determines executable edit processing for the object on the basis of a combination of a user and a device used by the user. Further, when an instruction has been issued to newly generate a report on each series or when an instruction has been issued to change or delete the contents of the report on each series, the determination unit 55 determines whether to reflect, for example, the generation of a new report on each series in the object on the basis of the edit processing determined as executable. Still further, the determination unit 55 specifies the contents of the object targeted for edit processing on the basis of a combination of the edit processing executable for the specified object and each device.

Figure 8:
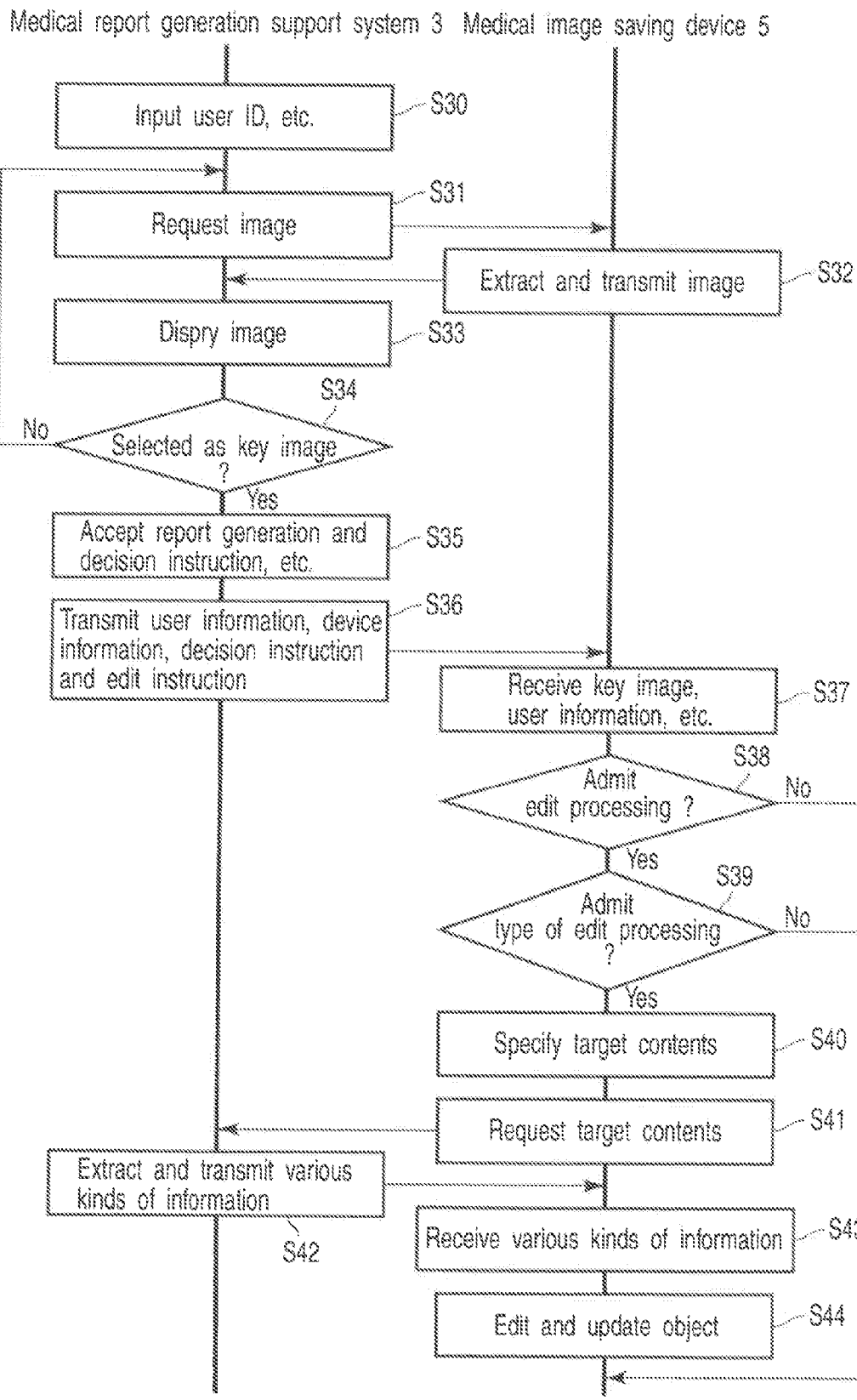
FIG. 8 is a flowchart showing the flow of image diagnosis support processing according to the second embodiment.

FIG. 8 is a flowchart showing the flow of image diagnosis support processing according to the second embodiment. As shown, the user who has generated the report first inputs, for example, his own ID to log into the medical report generation support system 3, and also inputs a UID of the examination targeted for report generation, thereby acquiring information necessary for the report generation (e.g., personal data on the patient) via the network N (step S30).

Then, a request for an image for use in the report generation is transmitted from a transmission/receiving unit 37 of the medical report generation support system 3 to a transmission/receiving unit 54 of the medical image saving device 5 (step S31). A control unit 58 searches a data saving unit 51 with reference to location specifying information, and extracts the requested image and transmits the image to the medical report generation support system 3 (step S32). In the medical report generation support system 3, the transmitted image is displayed and determined as to whether this image is used as the key image (steps S33, S34). When this image is determined not to be used as the key image, the processing from step S31 to step S34 is repeatedly performed. Moreover, when this image is determined to be used as the key image, the processing from step S31 to step S34 is also repeatedly performed as required if, for example, a further search for the key image is performed.

When the selection and determination of the key image have been finished in step S34, a report generating unit 31 generates a report on the basis of the input from the user, and receives an instruction to decide the contents of the report and an instruction on the edit processing for the processing of the key image (i.e., an instruction on any one of "new", "update" and "addition") via, for example, a GUI provided in an operation unit 39 (step S35). When, for example, the decision instruction is input, the transmission/receiving unit 37 transmits user information, information on the relevant device, a report decision instruction and a report edit instruction to the medical image saving device 5 (step S36).

In addition, a trigger for the transmission of the user information, etc. to the medical image saving device 5 is not restricted to the above-mentioned processing of deciding the report contents, and may be any trigger as long as it is an operation in which the user himself intentionally instructs to decide the key image. For example, it may be an operation of determining a particular image displayed in the medical report generation support system 3 or the medical image observation device 4 to be the key image (e.g., the operation of the decision button), an operation to affix the image to the report, or an operation of associating the image with report sentences (hyperlink).

When the user information, etc. are received by the transmission/receiving unit 54 (step S37), the determination unit 55 determines, in accordance with a combination of the user information and the device information and in accordance with an edit processing table, whether to admit the edit processing for this combination (step S38). For example, when the combination of the user information and the device information is "Dr. A" and "medical report generation support system", the determination unit 55 determines the edit processing to be admitted because the edit processing table designates the two types "update" and "addition" as admissible in this combination, thus proceeding to the next step. On the other hand, when the combination of the user information and the device information is, for example, "Dr. C" and "medical image observation device", the determination unit 55 determines that no edit processing can be admitted because the edit processing table defines no edit processing in this combination, such that the image diagnosis support processing is finished.

Then, when judging to admit the edit processing for the received combination, the determination unit 55 determines whether to admit the type of the received edit processing on the basis of whether the type of a report edit instruction received from the medical report generation support system 3 is defined as admissible in the edit processing table (step S39). That is, in the case where the combination of the user information and the device information is, for example, "Dr. A" and "medical report generation support system", when the type of the received report edit instruction is "update", the determination unit 55 determines the type of the received edit processing to be admitted because the "update" is defined in the edit processing table, and the determination unit 55 admits this edit instruction. On the other hand, when the type of the received report edit instruction is, for example, "new", the determination unit 55 determines the type of the received edit processing not to be admitted because the "new" is not defined in the edit processing table, and the determination unit 55 terminates this image diagnosis support processing.

When the type of the edit instruction is admitted, the determination unit 55 specifies the contents targeted for edit processing on the basis of the combination of the device information and the edit instruction and on the basis of a contents target table (step S40). For example, when the device is the "medical report generation support system" and the edit instruction is "change", the "(key) image UID", "device kind", "report UID" and "history management number" are targeted for edit processing. The transmission/receiving unit 54 transmits a request for the specified target contents to the medical report generation support system 3 (step S41). A report information collecting unit 33 of the medical report generation support system 3 extracts various kinds of information corresponding to the target contents. The extracted various kinds of information are transmitted to the medical image saving device 5 by the transmission/receiving unit 37 (step S42).

A management unit 56 of the medical image saving device 5 receives various kinds of information corresponding to the target contents from the medical report generation support system 3 (step S43), and, on the basis of the various kinds of information, edits the contents of the information on the key image included in the object (a plurality of objects in some cases) corresponding to the report in accordance with the admitted type of edit processing. The management unit 56 then overwrites the edited information to update the object (step S44).

(Effects)

The following effects can be obtained according to the configuration described above.

According to the present image diagnosis support system, the admission of the editing of the information on the key image of the object, the type of the edit processing, and the contents targeted for edit processing are controlled in accordance with a combination of the user information and the device information (i.e., a scene where the key image is used). Therefore, for example, even if there is a change in or addition to the image linked to the report, the edit processing table, for example, is defined to give priority to the instruction from the superior user who has the right to finally decide the key image, such that it is possible to automatically conform the image actually treated as the key image during the generation of the report to the key image specified by information on the key image in the object, thereby enabling a highly reliable object to be generated. Consequently, the key image in the past examination can be rapidly and accurately specified using the object at the time of, for example, imaging or interpretation and a diagnosis, and it is also possible to prevent an error caused by the confusion of key images.

THIRD EMBODIMENT

Next, a third embodiment is described. In the image diagnosis support system according to the second embodiment, after an instruction to edit a key image has been issued on the side of the medical report generation support system 3, the medical image saving device 5 determines and controls/manages the admission of the edit processing, the type of the edit processing and the contents targeted for edit processing. In contrast, in an image diagnosis support system according to the present embodiment, before an instruction to edit a key image is issued on the side of a medical report generation support system 3, a medical image saving device 5 determines the admission of the edit processing, etc. in accordance with a combination of user information and device information, and the result of the determination is provided to the side of the medical report generation support system 3.

That is, the medical image saving device 5 receives the user information and the device information, for example, at the stage of receiving a request to acquire an image in step S31 of FIG. 8 (i.e., at the stage before an instruction to edit the key image), and the processing from step S38 to step S41 is performed accordingly. This enables, for example, a report creator to know the admission of the edit processing of the key image, the type of the edit processing and the contents targeted for edit processing, for example, before the generation of a report.

It is to be noted that the present invention is not totally limited to the embodiments described above, and modifications of components can be made and embodied at the stage of carrying out the invention without departing from the spirit thereof. For example, there are the following specific modifications:

(1) The functions according to the present embodiments can also be achieved by installing programs for executing the processing in a computer in, for example, a workstation and uncompressing the programs on a memory. In this case, the programs capable of causing the computer to execute this method can be distributed after stored in a recording medium such as a magnetic disk (such as a floppy (registered trademark) disk or a hard disk), an optical disk (such as a CD-ROM or a DVD) or a semiconductor memory.

(2) In the configurations of the embodiments described above, the GUI provided in the operation unit 39, for example, is used to input an instruction on the kind of edit processing to be performed for each object targeted for the management of the examination corresponding to the report (i.e., an instruction on the type of edit processing). However, the form of the instruction on the edit processing of the object is not limited to this, and, for example, it is also possible to employ a configuration in which any one kind of the edit processing: new, update and addition is automatically selected in conjunction with the right of the user of the report.

Furthermore, suitable combinations of a plurality of components disclosed in the embodiments described above permit various inventions to be formed. For example, some of all the components shown in the embodiment described above may be eliminated. Further, the components in different embodiments may be suitably combined together.

What is claimed is:

1. An image diagnosis support system, comprising:
a non-transitory memory that stores a plurality of objects including, as contents thereof, information on a diagnostic image serving as a basis in a diagnosis based on an examination, the memory also storing a first table to manage admission of edit processing of information on the diagnostic image included in the object for each combination of user information to specify a user involved in the generation of a medical report and device information to specify a device used for the generation of the medical report;
an acceptance unit configured to accept the user information and the device information from the device involved in the generation of the medical report;
a determination unit configured to determine, based on information included in the first table for various combinations of the user information and device information, whether to admit the edit processing of the information on the diagnostic image included in the object with regard to the combination of the accepted user information and the device information; and
a transmission unit configured to transmit the result of the determination to the device involved in the generation of the medical report.

2. The image diagnosis support system according to claim 1, further comprising:
an information generating unit configured to generate edit information regarding the diagnostic image in response to an instruction to identify the diagnostic image from the device involved in the generation of the medical report, when the determination unit determines to admit the edit processing,
wherein the acceptance unit is configured to accept examination specifying information to specify an examination or series corresponding to the medical report, and the edit information, the system further comprising
an editing unit configured to edit and update information on the diagnostic image in the object corresponding to the examination specified by the examination specifying information, in accordance with the edit information.

3. The image diagnosis support system according to claim 2, wherein the edit information includes at least one of parameter setting values concerning the addition of a new diagnostic image, the deletion of the existing diagnostic image, a change to another diagnostic image, and image processing of the diagnostic image.

4. The image diagnosis support system according to claim 2, wherein the edit information includes a type of edit processing;
the first table further defines an admissible type of edit processing of the information on the diagnostic image for each combination of the user information and the device information;
the determination unit is configured to determine the type of edit processing included in the accepted edit information by use of the accepted user information and device information and by use of the first table, and to determine whether to admit processing included in the edit information based on the determined type of edit processing; and
the editing unit is configured to edit, in accordance with the type of edit processing included in the edit information, the information on the diagnostic image in the object specified by the accepted examination specifying information when the determination unit determines to admit the processing included in the edit information.

5. The image diagnosis support system according to claim 4, further comprising:
an input unit to input the type of edit processing.

6. The image diagnosis support system according to claim 5, wherein the memory further stores a second table to define edit processing target information for each type of edit processing;
when judging to admit the edit processing instruction, the determination unit is configured to specify edit processing target information based on the edit processing instruction and the second table; and
the editing unit is configured to edit the specified target information.

7. The image diagnosis support system according to claim 2, wherein the edit processing is any one of processing to newly register information on the diagnostic image, processing to replace already registered information on the diagnostic image with information on another diagnostic image, and processing to add new information to the already registered information on the diagnostic image.

8. The image diagnosis support system according to claim 2, wherein the acceptance unit is configured to accept an instruction to edit the information on the diagnostic image only when receiving information indicating the identification of the diagnostic image from a device to which the edit instruction has been input.

* * * * *